United States Patent [19]

Duffett

[11] Patent Number: Plant 5,810

[45] Date of Patent: Nov. 25, 1986

[54] CHRYSANTHEMUM PLANT NAMED ELFIN

[75] Inventor: William E. Duffett, Salinas, Calif.

[73] Assignee: Yoder Brothers, Inc., Barberton, Ohio

[21] Appl. No.: 636,504

[22] Filed: Aug. 1, 1984

[51] Int. Cl.[4] ..... A01H 5/00

[52] U.S. Cl. ..... Plt./76

[58] Field of Search ..... Plt./76, 80

*Primary Examiner*—R. E. Bagwill

*Attorney, Agent, or Firm*—Schwartz, Jeffery, Schwaab, Mack, Blumenthal & Evans

[57] ABSTRACT

A Chrysanthemum plant named Elfin characterized as to uniqueness by the combined characteristics of small pompon capitulum form, formal decorative capitulum type, light red-purple ray floret color, diameter across face of capitulum ranging from 4.5 to 5.5 cm. at maturity, uniform nine week flowering response, medium plant height when grown single stem, 15 to 20 cm. peduncles on open, normally terminal sprays, and 13° C. minimum temperature tolerance for initiation and development of flowering buds with rapid flowering down the stem.

3 Drawing Figures

1

The present invention comprises a new and distinct cultivar of *Chrysanthemum morifolium,* Ramat., named Elfin.

Elfin is a product of a planned breeding program which had the objective of creating new Chrysanthemum cultivars for cut spray mum programs having low temperature tolerance, formal decorative capitulum type, purple ray floret color, eight to nine week flowering response, and the ability to produce commercially acceptable quality in year round programs. Such traits in combination were not present or needed improvement in previously available commercial cultivars.

Elfin, identified as 81821001, was originated from a cross made by William E. Duffett in a controlled breeding program in Salinas, Calif. in 1980. The female parent, identified as 78161006, was an unnamed seedling. The male parent, identified as 78945008, was also an unnamed seedling.

Elfin was discovered and selected as one flowering plant within the progeny of the stated cross by William E. Duffett on Nov. 6, 1981 in a controlled environment in Bogota, Colombia.

The first act of asexual reproduction of Elfin was accomplished when vegetative cuttings were taken from the initial selection in January 1982 in a controlled environment in Bogota, Colombia by a technician working under formulations established and supervised by William E. Duffett through Fernando Jaramillo.

Horticultural examination of selected units initiated Sept. 21, 1982 has demonstrated that the combination of characteristics as herein disclosed for Elfin are firmly fixed and are retained through successive generations of asexual reproduction.

Elfin has not been observed under all possible environmental conditions. The phenotype may vary significantly with variations in environment such as temperature, light intensity, and day length. The following observations, measurements and comparisons describe plants grown in Bogota, Colombia under greenhouse conditions which approximate those generally used there in commercial practice.

The following traits have been repeatedly observed and are determined to be basic characteristics of Elfin which in combination distinguish this Chrysanthemum as a new and distinct cultivar:

2

1. Small pompon capitulum form.
2. Formal decorative capitulum type.
3. Light red-purple ray floret color.
4. Diameter across face of capitulum ranging from 4.5 to 5.5 cm. at maturity.
5. Uniform nine week photoperiodic flowering response to short days.
6. Medium peduncle length, ranging from 15 to 20 cm.
7. Medium plant height, requiring two long day weeks prior to short days to attain a flowered plant height of 90 to 95 cm. for year around flowering.
8. Low temperature tolerance of 13° C. for initiation and development with rapid flowering down the stem when grown in single stem cut spray programs with a continuous dark period of 12 hours.

The accompanying photographic drawings show typical inflorescence and leaf characteristics of Elfin, with the colors being as nearly true as possible with illustrations of this type.

Sheet 1 is a color photograph of Elfin grown as a single stem cut spray.

Sheet 2 is a black and white photograph of three views of the inflorescence of Elfin.

Sheet 3 is a black and white photograph showing the upper surface and under surface of the leaves of Elfin at three stages of development (mature, intermediate and immature).

Of the many commercial cultivars known to the present inventor, the most similar in comparison to Elfin is Pink Dot, an unpatented, commercially available cultivar. Reference is made to attached Chart A which compares certain characteristics of Elfin to those same characteristics of Pink Dot. Elfin develops a lighter, smoother ray floret color with less color contrast between the upper and under surfaces. The form, type, peduncle length, inflorescence size, plant height, response and low temperature tolerance of Elfin are similar to those same characteristics of Pink Dot.

In the following description, color references are made to The Royal Horticultural Society Colour Chart. The color values were determined between 9:45 A.M. and 10:00 A.M. on Dec. 27, 1983 under 380 foot-candle light intensity at Salinas, Calif.

Classification:

*Botanical.*—*Chrysanthemum morifolium,* Ramat., cv Elfin.

*Commercial.*—Small decorative cut spray mum.

I. INFLORESCENCE

A. Capitulum:

*Form.*—Small pompon.

*Type.*—Formal decorative.

*Diameter across face.*—4.5 to 5.5 cm.

B. Corolla of ray florets:

*Color (general tonality from a distance of three meters).*—Light red-purple.

*Color (upper surface).*—69A to 69B with longitudinal margins of the floret 69C.

*Color (under surface).*—69B at the tip of the floret to 69D at the base of the floret.

*Shape.*—Short, broad. Rounded tip.

C. Corolla of disc florets:

*Color (mature).*—154A.

*Color (immature).*—160A.

D. Reproductive organs:

*Androecium.*—Present disc florets only; moderate pollen.

*Gynoecium.*—Present both ray and disc florets.

II. PLANT

A. General appearance:

*Height.*—Medium; 90 to 95 cm., as a flowering plant from a rooted cutting, with fourteen long days for year around flowering maintaining a minimum nightly 12 hour continuous dark period.

B. Foliage:

*Color (upper surface).*—147A.

*Color (under surface).*—147B.

*Shape.*—Deep narrow lobes and moderately serrated.

CHART A

COMPARISON OF ELFIN AND PINK DOT

| CULTIVAR | RAY FLORET COLOR | CAPITULUM FORM AND TYPE | SPRAY FORMATION |
|---|---|---|---|
| ELFIN | LIGHT RED-PURPLE | SMALL POMPON FORMAL DECORATIVE | 15 to 20 cm. PEDUNCLES |
| PINK DOT | LIGHT VIOLET | SMALL POMPON FORMAL DECORATIVE | 15 to 20 cm. PEDUNCLES |

| CULTIVAR | DIAMETER ACROSS FACE OF CAPITULUM | PLANT HEIGHT | FLOWERING RESPONSE PERIOD | LOW TEMPERATURE TOLERANCE |
|---|---|---|---|---|
| ELFIN | 4.5 to 5.5 cm. | MEDIUM 90 to 95 cm. | 9 WEEKS | 13° C. |
| PINK DOT | 4.0 to 5.0 cm. | MEDIUM 90 to 95 cm. | 9 WEEKS | 13° C. |

COMPARISONS MADE OF PLANTS GROWN AS SINGLE STEM CUT SPRAY MUMS WITH 14 LONG DAYS IN BOGOTA, COLUMBIA

I claim:

1. A new and distinct plant of *Chrysanthemum morifolium,* Ramat., named Elfin, as described and illustrated, and particularly characterized as to uniqueness by the combined characteristics of small pompon capitulum form; formal decorative capitulum type; light red-purple ray floret color; diameter across face of capitulum ranging from 4.5 to 5.5 cm. at maturity; uniform nine week flowering response; medium plant height when grown single stem; 15 to 20 cm. peduncles on open, normally terminal sprays; and 13° C. minimum temperature tolerance for initiation and development of flowering buds with rapid flowering down the stem.

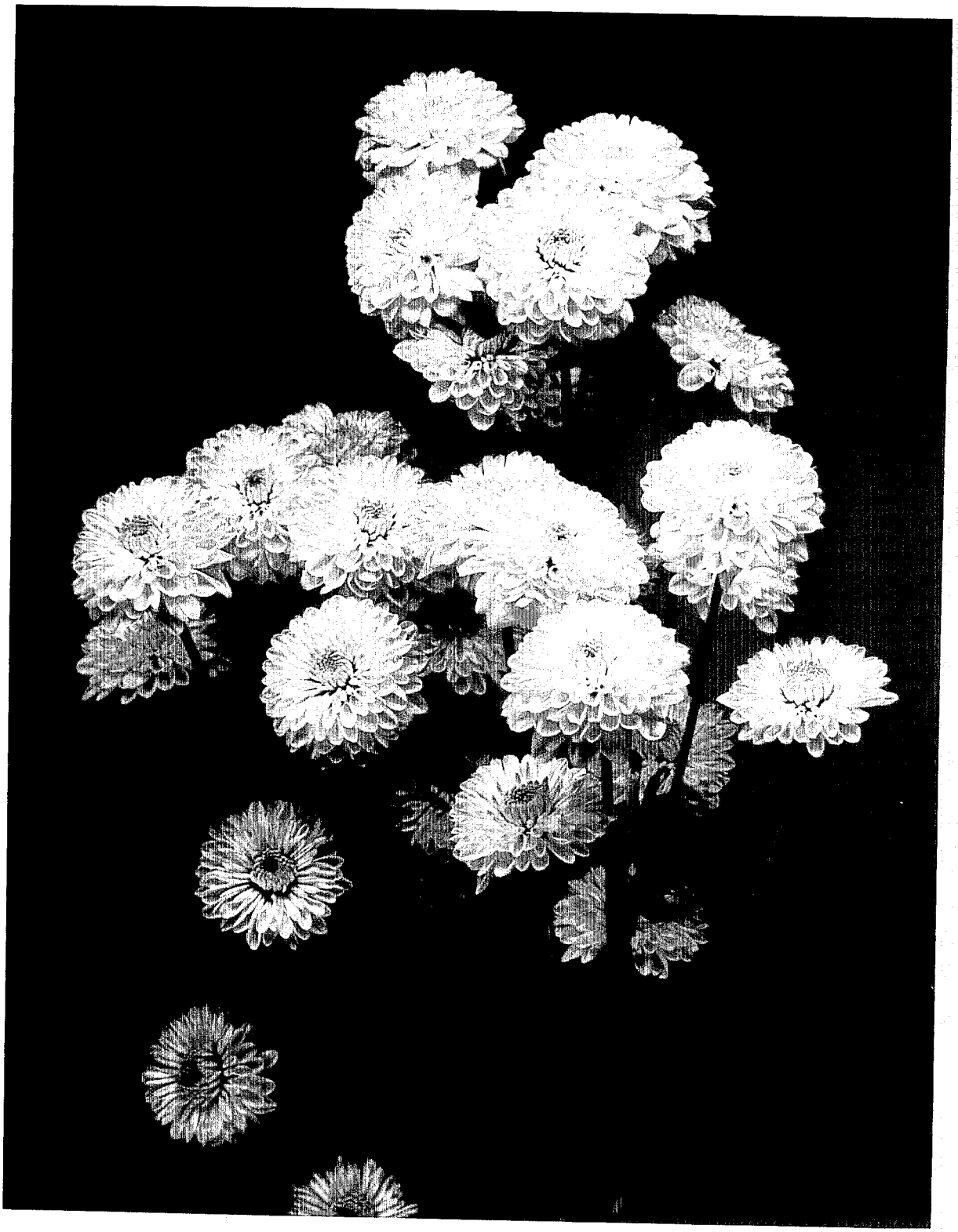

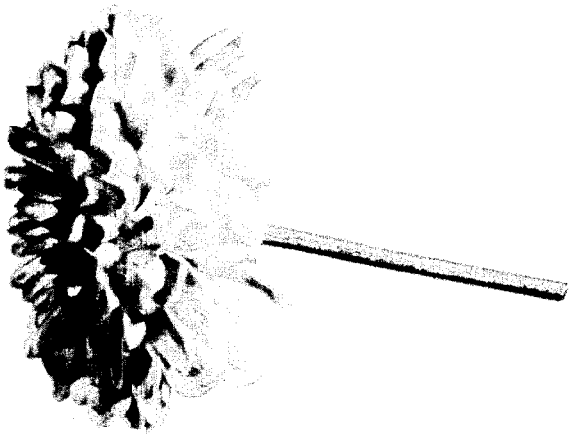
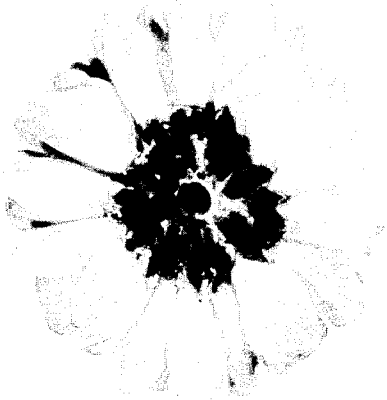
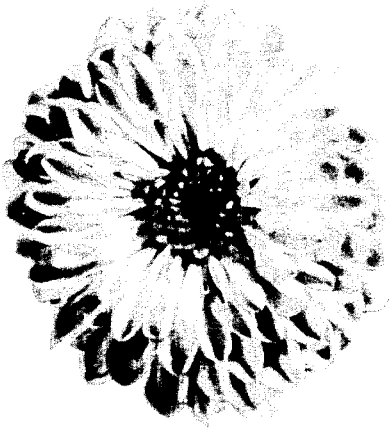

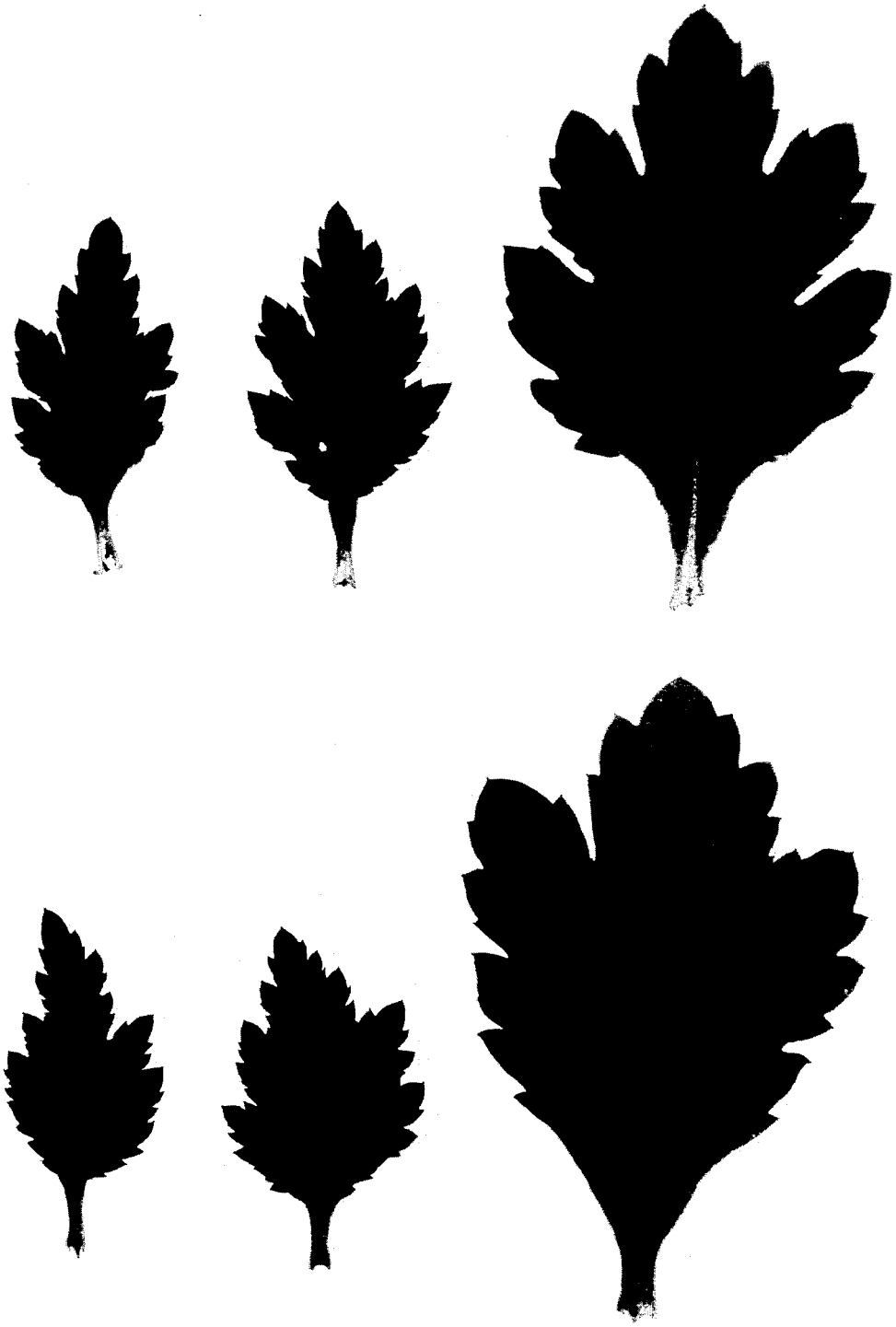

* * * * *